US008603153B2

(12) United States Patent
Haverkost (10) Patent No.: US 8,603,153 B2
(45) Date of Patent: Dec. 10, 2013

(54) METHOD AND SYSTEM FOR FIXATION OF ENDOLUMINAL DEVICES

(75) Inventor: Patrick A. Haverkost, Brooklyn Center, MN (US)

(73) Assignee: Lifeshield Sciences, LLC, Plano, TX (US)

(*) Notice: Subject to any disclaimer, the term of this patent is extended or adjusted under 35 U.S.C. 154(b) by 1886 days.

(21) Appl. No.: 11/067,938

(22) Filed: Feb. 28, 2005

(65) Prior Publication Data

US 2005/0143804 A1 Jun. 30, 2005

Related U.S. Application Data

(62) Division of application No. 09/978,895, filed on Oct. 17, 2001, now abandoned.

(51) Int. Cl.
*A61F 2/06* (2013.01)

(52) U.S. Cl.
USPC ........................................... 623/1.15

(58) Field of Classification Search
USPC ........ 606/192, 194, 198; 623/1.11–1.15, 1.35
See application file for complete search history.

(56) References Cited

U.S. PATENT DOCUMENTS

| 5,064,435 | A | * | 11/1991 | Porter | 623/23.7 |
| 5,415,664 | A | | 5/1995 | Pinchuk | |
| 5,489,295 | A | | 2/1996 | Piplani et al. | |
| 5,522,880 | A | * | 6/1996 | Barone et al. | 128/898 |
| 5,609,605 | A | * | 3/1997 | Marshall et al. | 623/1.11 |
| 5,630,840 | A | | 5/1997 | Mayer | |
| 5,782,906 | A | | 7/1998 | Marshall et al. | |
| 5,824,037 | A | * | 10/1998 | Fogarty et al. | 623/1.13 |
| 5,824,040 | A | * | 10/1998 | Cox et al. | 623/1.35 |
| 5,843,176 | A | * | 12/1998 | Weier | 623/1.2 |

(Continued)

FOREIGN PATENT DOCUMENTS

| CA | 2267709 | 9/1999 |
| CA | 2392659 | 7/2001 |

(Continued)

OTHER PUBLICATIONS

International Search Report dated Jan. 22, 2003, from International Application No. PCT/US02/32545.

(Continued)

*Primary Examiner* — Thomas McEvoy
*Assistant Examiner* — Julie A Szpira
(74) *Attorney, Agent, or Firm* — Brooks, Cameron & Huebsch, PLLC (57) ABSTRACT

A system and method employs collar stents to implant an endoluminal device, such as a stent-graft, in a lumen. The system comprises at least one collar stent adapted to precondition a portion of the lumen for anchoring an endoluminal device having at least a portion adapted to be deployed radially within the collar stent. The method comprises first deploying one or more collar stents, and then deploying the endoluminal device radially within the one or more collar stents. In various embodiments, the collar stent may be radiopaque, may have inwardly protruding barbs for engaging the endoluminal device, and may have a region having a relatively low percentage of open area for bridging a portion of the main lumen having an intersecting lumen. The preconditioning step of implanting the collar stent may change the morphology of the lumen to more favorable morphology, such as from a non-circumferential geometry to a circumferential geometry.

18 Claims, 4 Drawing Sheets

(56) References Cited

U.S. PATENT DOCUMENTS

| | | | |
|---|---|---|---|
| 5,851,228 A * | 12/1998 | Pinheiro | 623/1.13 |
| 5,941,908 A * | 8/1999 | Goldsteen et al. | 623/1.23 |
| 5,984,955 A * | 11/1999 | Wisselink | 623/1.35 |
| 5,993,489 A | 11/1999 | Lewis et al. | |
| 6,066,167 A | 5/2000 | Lau et al. | |
| 6,077,296 A * | 6/2000 | Shokoohi et al. | 623/1.11 |
| 6,090,128 A | 7/2000 | Douglas | |
| 6,102,940 A | 8/2000 | Robichon et al. | |
| 6,123,723 A | 9/2000 | Kónya et al. | |
| 6,168,610 B1 * | 1/2001 | Marin et al. | 606/198 |
| 6,203,568 B1 * | 3/2001 | Lombardi et al. | 623/1.13 |
| 6,270,516 B1 | 8/2001 | Tanner et al. | |
| 6,334,866 B1 * | 1/2002 | Wall | 623/1.12 |
| 6,344,052 B1 * | 2/2002 | Greenan et al. | 623/1.1 |
| 6,344,056 B1 * | 2/2002 | Dehdashtian | 623/1.35 |
| 6,361,556 B1 | 3/2002 | Chuter | |
| 6,368,355 B1 | 4/2002 | Uflacker | |
| 6,395,022 B1 * | 5/2002 | Piplani et al. | 623/1.35 |
| 6,533,811 B1 * | 3/2003 | Ryan et al. | 623/1.23 |
| 6,613,078 B1 * | 9/2003 | Barone | 623/1.13 |
| 6,660,030 B2 | 12/2003 | Shaolian et al. | |
| 6,676,694 B1 | 1/2004 | Weiss | |
| 6,695,833 B1 | 2/2004 | Frantzen | |
| 6,860,900 B2 * | 3/2005 | Clerc et al. | 623/1.35 |
| 2002/0052643 A1 * | 5/2002 | Wholey et al. | 623/1.13 |
| 2004/0068277 A1 | 4/2004 | Solem | |

FOREIGN PATENT DOCUMENTS

| | | |
|---|---|---|
| EP | 0 781 528 | 7/1997 |
| FR | 2775182 | 8/1999 |
| WO | WO-01/49211 | 7/2001 |

OTHER PUBLICATIONS

Translation of Office Action in Japanese Application 2003-535677 mailed Jun. 10, 2008.

Canadian Office Action dated Dec. 14, 2009 for related Canadian Patent Application No. 2,469,458. 3 pgs.

Canadian Office Action in related Canadian Patent Application No. 2,469,452. Jun. 20, 2011. 9 pgs.

* cited by examiner

METHOD AND SYSTEM FOR FIXATION OF ENDOLUMINAL DEVICES

This application is a divisional application of U.S. patent application Ser. No. 09/978,895, filed on Oct. 17, 2001 now abandoned titled METHOD AND SYSTEM FOR FIXATION OF ENDOLUMINAL DEVICES.

TECHNICAL FIELD

This invention relates generally to endoluminal devices and, more specifically, to methods and apparatus for developing a secure attachment of an endoluminal device to the walls of a lumen in which it is implanted.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. As used herein, however, the term "stent" is a shorthand reference referring to a covered or uncovered such device.

A covered stent may be used, for example, to treat a vascular aneurysm by removing the pressure on a weakened part of an artery so as to reduce the risk of rupture. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to this access location, whereas the term "distal" is used to refer to portions farther from the access location.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Figure 1:
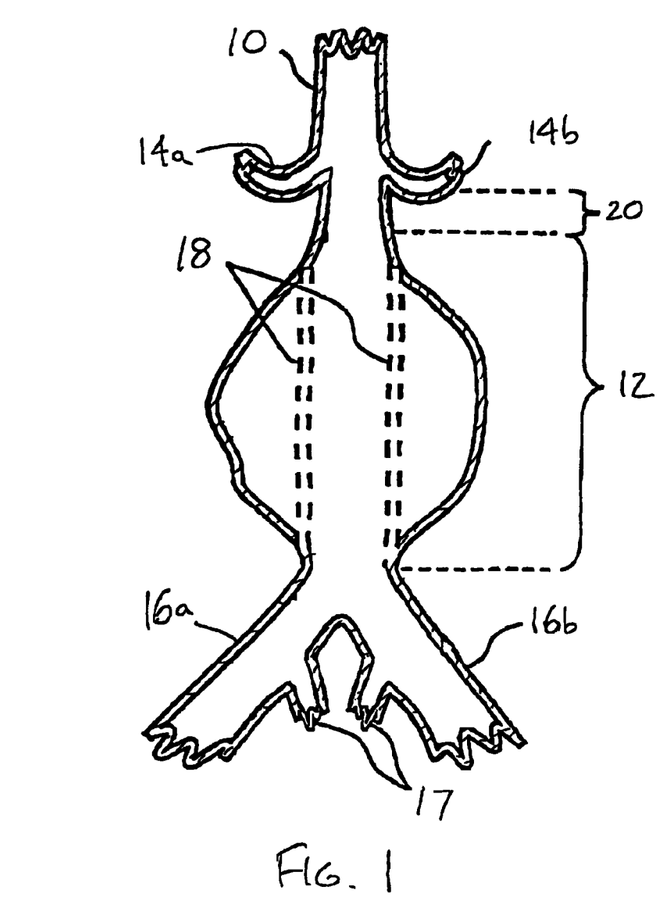
FIG. 1 is a longitudinal section illustration of an aorta with an aneurysm, as is commonly known in the art.

Among the many applications for stent-grafts is that of deployment in branching lumen, and more specifically in bifurcated lumen, such as for repair of abdominal aortic aneurysms (AAA). Various stent-graft configurations are known in the art for bifurcated applications. Referring now to FIG. 1, there is shown an illustration of the typical morphology of a human aorta 10 afflicted with an abdominal aortic aneurysm 12. An abdominal aortic aneurysm 12 is typically located proximally of renal arteries 14a and 14b and distally of branching iliac arteries 16a and 16b. Arteries 16a and 16b are typically referred to as "external" iliac arteries, whereas arteries 17 are typically referred to as "internal" iliac arteries. The location of normal (not afflicted with an aneurysm) aortic walls 18 are shown with dashed lines. The portion of aorta 10 between aneurysm 12 and renal arteries 14a and 14b as shown in FIG. 1 is referred to herein as neck 20. The neck is typically a critical fixation zone for stent-grafts placed to repair abdominal aortic aneurysms. Poor fixation may allow blood flow around the stent-graft, which can put pressure on the aneurysmal wall.

A substantial percentage of patients have necks that are non-circumferential. Others may have calcification in the neck. Non-circumferential or calcified necks may impede proper fixation of the stent-graft. In some patients, the aorta is angled and may have an inflection point in the portion of the neck where the stent-graft needs to be affixed. Still other patients exhibit a neck length of 1.5 mm or less and have historically not been considered good candidates for stent-grafts because of insufficient fixation area for the distal end of the stent-graft.

Even when a stent-graft is implanted in an aorta with acceptable morphology, over time after implantation of a stent-graft, the aneurysm may become weaker, resulting in morphological changes due to shrinkage of the diseased and surrounding tissues. Changes in anatomy may cause a stent-graft to bend or even kink, and may also cause the neck portion of the stent-graft to migrate into the area of the aneurysm, which may result in the leakage of blood around the graft.

Finally, placement of AAA stent-grafts typically requires great skill and proper hospital equipment to enable the desired precision. In particular, effective viewing systems are often advantageous to enable vision of the implantation procedure. Some hospitals have better viewing equipment than others. Placement inaccuracies can result in post-procedure complications for the patient. Accordingly, it is desirable to provide good vision of the deployment area during implantation of any stent-graft.

Thus, as discussed above, there are a number of ways in which fixation of a stent-graft may be problematic. It is therefore desirable to provide a method and apparatus that overcomes or at least mitigates many of the difficulties noted above, and provides more accurate and effective fixation of stent-grafts. The need for improved fixation is not limited only to AAA stent-graft applications for difficult morphologies, but may extend to processes for implantation of any type of endoluminal device anywhere in the body, even in routine morphologies.

SUMMARY OF THE INVENTION

In accordance with this invention, there is provided a method for deploying an endoluminal device in a lumen. The method comprises the steps of first deploying one or more collar stents in one or more anchor locations in the lumen, and then deploying the endoluminal device radially within the one or more collar stents. The method may further comprise providing a period of time, such as about 2 weeks, between implantation of the collar stents and deployment of the endoluminal device, sufficient to allow intravascular tissue growth around the one or more collar stents to further strengthen the anchor location. The method is particularly useful for implanting a stent-graft, such as an AAA stent-graft, having a distal end adapted to be deployed upstream of the proximal ends of the stent-graft, the method comprising implanting a first of the collar stents in a first anchor location aligned with the distal end of the stent-graft, a second collar stent in a second anchor location aligned with a first proximal end, and a third collar stent in a third anchor location aligned with a second proximal end of the stent-graft.

According to an embodiment of the present invention, the deployment method includes the steps of deploying a collar stent and then allowing passage of a sufficient period of time for intravascular tissue growth to fill-in the gap between the collar stent and the lumen wall before deploying the endoluminal device radially within the collar stents. In many cases, this will increase the amount of available fixation length in an anchor location for fixation of an endoluminal device to a lumen wall. This method may thus make implantation of an endoluminal device an option that is not otherwise available for patients with an inadequate amount of available fixation length.

In one embodiment, the first collar stent comprises a first region having a first stent geometry with a first percentage of open area, a second region having a second stent geometry with a second percentage of open area greater than the first percentage, and a third region having the third stent geometry with a third percentage of open area less than the second percentage, the second region located intermediate the first region and the third region. In such embodiment, the method may comprise implanting the first collar stent so that the second region bridges a portion of the lumen where one or more branch lumen intersect the lumen.

The collar stent may also comprise a plurality of barbs that protrude radially inward from the stent. In such an embodiment, the method comprises implanting the endoluminal device so that the barbs engage the endoluminal device.

The invention comprises any method comprising preconditioning a portion of the lumen by implanting a collar stent prior to implanting the stent-graft, and then implanting the stent-graft so that at least a portion of the stent-graft axially overlaps the collar stent. The preconditioning step may change a first morphology of the lumen to a second, more favorable morphology. For example, where the lumen at the anchor location is non-circumferential, the method comprises implanting the collar stent to conform the anchor location to a circumferential geometry. Where the lumen at the anchor location has an angular inflection, the method comprises implanting the collar stent to straighten the angular inflection. The collar stent may have a greater radiopacity than the lumen such that implantation of the collar stent enhances viewability of the portion of the lumen.

The invention also comprises a system for implantation of an endoluminal device in a lumen. The system comprises at least one collar stent adapted to precondition a portion of the lumen for anchoring the endoluminal device, and the endoluminal device having at least a portion adapted to be deployed radially within the collar stent. The collar stent may be radiopaque. The collar stent may have a radial strength sufficient to modify a morphology of the lumen into which it is adapted to be implanted, such as to change a non-circumferential morphology to a circumferential morphology, to change an angularly inflected morphology to a straight morphology, or both.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 2:
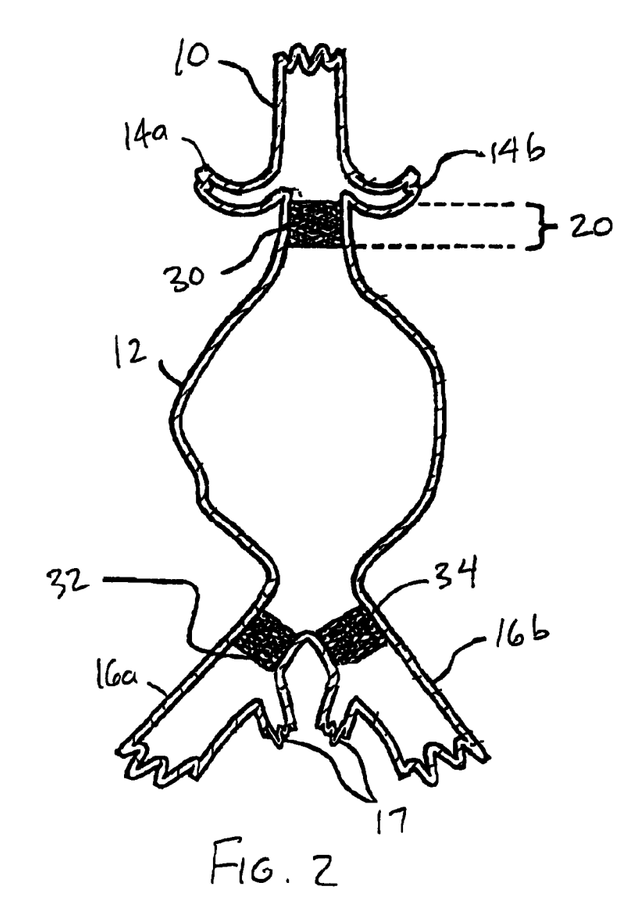
FIG. 2 shows the aorta of FIG. 1 with a set of collar stents implanted therein in accordance with the invention.

The invention comprises a method and apparatus for improved fixation of endoluminal devices. The method comprises preconditioning the lumen prior to implantation of the endoluminal device, by implanting one or more collar stents, and then deploying the endoluminal device on top of the collar stents. Referring now to FIG. 2, there is shown an illustration of the aorta 10 after being preconditioned with a plurality of collar stents 30, 32, and 34 placed in anchor locations in the lumen. Collar stent 30 is mounted in neck 20 and collars 32 and 34 are mounted in iliac arteries 16a and 16b, respectively. Neck collar stent 30 is typically a bare (non-covered) wire stent with a diameter of about 12 mm to about 40 mm and a length of about 15 mm to about 65 mm. Iliac collar stents 32 and 34 are typically also made of wire and have a diameter of about 5 mm to about 20 mm, and a length of about 15 mm to about 65 mm. The collar stents are not limited to any particular dimensions or materials of construction, however, and at least portions may be covered or lined, if desired. These stents serve as a platform for the subsequent placement of a stent-graft or other device.

Figure 3:
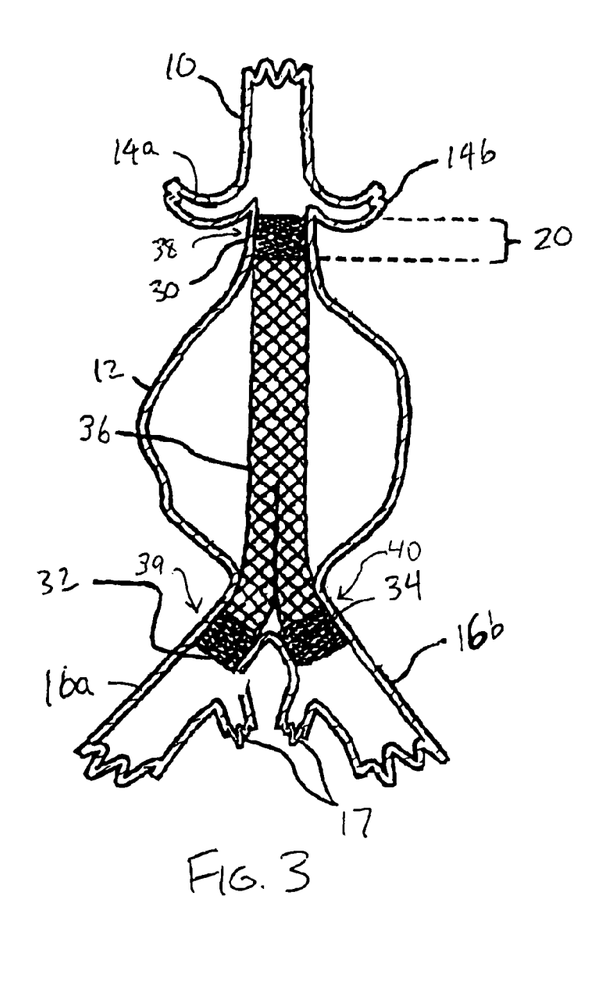
FIG. 3 shows the aorta of FIGS. 1 and 2 with a stent-graft deployed radially within the collar stents in accordance with the invention.

FIG. 3 shows the same aorta 10 after implantation of an endoluminal device, in this case stent-graft 36, radially within collar stents 30, 32, and 34. Stent-graft 36 has a distal end 38 and two proximal ends 39 and 40. Distal end 38 engages collar stent 30, while proximal ends 39 and 40 engage collar stents 32 and 34, respectively. Although shown in FIG. 3 with the collar stents engaged with the ends of stent-graft 36, the collar stents may be placed in any location in the lumen to which it is desired to anchor the endoluminal device to the wall of the lumen. Collar stents 30, 32, and 34, as well as stent-graft 36 may be implanted by any, preferably minimally-invasive, technique known in the art. Thus, in the final configuration, the stent-graft 36 can be said to be radially within the collar stents 30, 32, and 34 because at the portions where the stent-graft axially overlaps the collar stents, the stent-graft is radially within the collar stents. At these points, the stent-graft 36 engages the collar stents 30, 32, and 34 either by a direct frictional engagement, by an indirect engagement through intravascular tissue growth, or in some other manner. The language "radially within" shall encompass any endoluminal device having this characteristic, even if the stent-graft has a diameter at some point along its length greater than the diameter of the collar stents.

Figure 4:
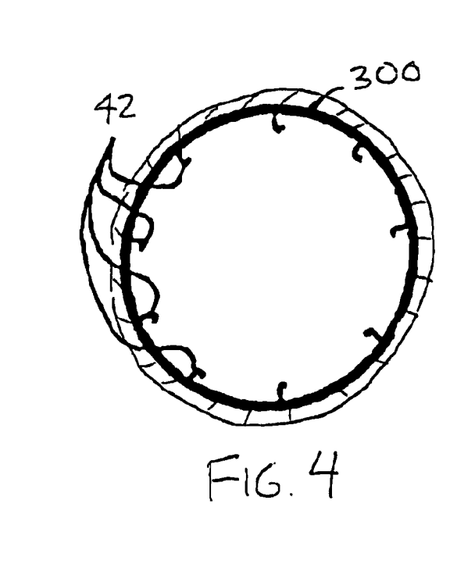
FIG. 4 shows an axial view of an exemplary, collar stent of the invention having internal barbs.
Figure 5:
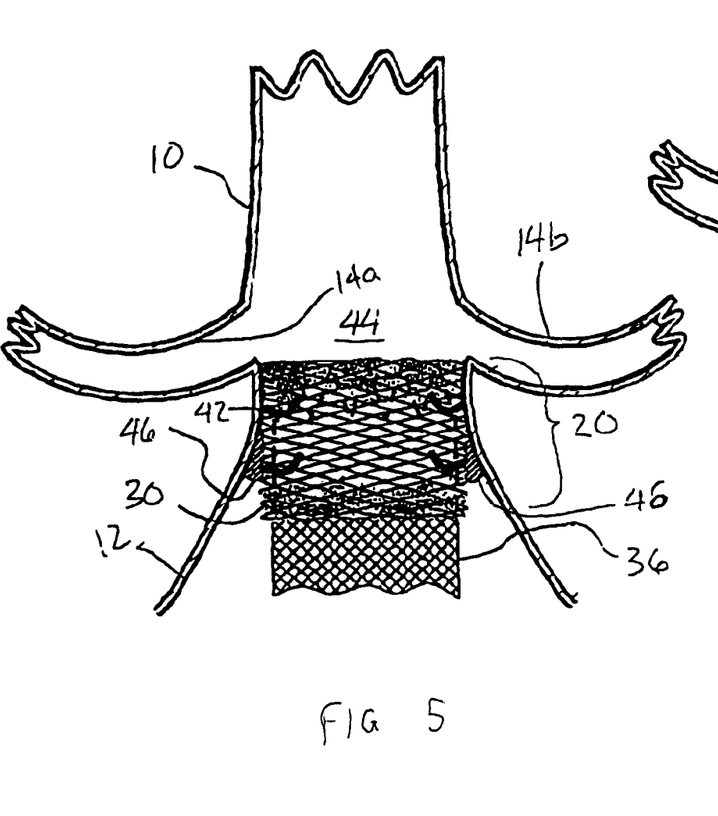
FIG. 5 shows a distal portion of an aorta in longitudinal section after an exemplary collar stent has been implanted therein for a period of time sufficient to allow intravascular tissue growth to grow.

FIG. 4 shows an axial view of a typical collar stent 300. Stent 300 has a plurality of optional barbs 42 that protrude radially inward. Barbs 42 are mechanically connected to collar stent 300. Where collar 300 has a cut hypotube architecture, one or more of the stent features may be bent inward to create a barb. Where collar stent 300 is a woven stent such as a Wallstent, the barbs may be added by, for example, incorporating additional wires into the braid and forming the barbs with the additional wires, as is well known in the art. The stent may also have a plurality of barbs (not shown) that protrude radially outward for enhanced fixation of the collar to the body lumen, as are known in the art. The methods of creating internal barbs 42 may be any method for creating external barbs known in the art. The barbs that protrude radially inward engage and anchor the endoluminal device, such as stent-graft 36, when it is later deployed radially within the collar, as shown in FIG. 5. The barbs may be particularly useful for anchoring the endoluminal device to the collar stent or collars until intravascular tissue growth secures the endoluminal device. Similarly, the endoluminal device, such as stent-graft 36, may have external barbs, such as are known in the art, for anchoring the endoluminal device to the collar stent or to any intravascular tissue growth over the collar stent.

FIG. 5 further illustrates how the collar stent of this invention may help to increase the available fixation length in a particular anchor location in a lumen. As shown in FIG. 5, aneurysm 12 begins so close to renal intersection 44 that the neck 20 has a diameter that flares outwardly almost immediately downstream of the renal arteries 14a and 14b. By first placing collar stent 30 in neck 20 and allowing intravascular tissue growth 46 between the lumen walls and the collar, the available fixation length in the neck is, in effect, lengthened. The collar stent thus establishes a more uniform, predictable, and measurable platform for later placement of stent graft 36. The period of time between implantation of collar stent 30 and stent-graft 36 may preferably be on the order of about 2 weeks to allow sufficient intravascular tissue growth. Longer or shorter periods may be used, however, as desirable for individual applications.

Thrombotic response pathology is predictable and documented for bare stents within a vascular treatment area, which can be used to the advantage of the practitioner for determining the appropriate length of time after collar implantation to proceed with deployment of the endoluminal device radially within the collar or collars. The collar stents of the present invention may thus be uncoated to encourage intravascular tissue growth, or may be treated with special coatings known in the art for encouraging intravascular tissue growth even more. In some cases, for example, approximately 1 mm of intravascular tissue growth may occur on a bare metal stent. As used herein, the term "intravascular tissue growth" may comprise thrombus, hyperplasia, calcium, inflammation or inflammatory cells, general cell tissue (i.e. blood, cells, platelets, clots, etc.), fibren, and/or foreign material. The intravascular tissue growth provides a predictable platform upon which to anchor a stent-graft. This growth occurs even when a collar stent is placed over a calcium deposit on a lumen wall. Thus, the use of a collar stent provides not only a more circumferential morphology when placed over a calcium deposit, because of the intravascular tissue growth in the gap between the lumen wall and the stent caused by the presence of the deposit, but further provides a uniformly textured wall of intravascular tissue growth into which the subsequent endoluminal device may be placed.

If the endoluminal device deployed radially within the collar stent is also bare metal, an additional 1 mm of intravascular tissue growth may occur. Thus, the lumen into which the collar stents are implanted may lose as much as 4 mm in diameter due to intravascular tissue growth alone. Thus, it may be advantageous to choose materials for the collar stent that are particularly thin. Thus, radial strength achieved through a dense architecture of relatively thin elements may be preferred to a more sparse architecture of relatively thick elements. A balloon-expandable, laser-cut hypotube architecture may provide a desirable combination of relatively thin, yet relatively high compressive strength elements. The collar stent also typically has a sufficient tensile strength to withstand any stresses put on the collar stent by any forces that may pull on the stent-graft.

Thus, as shown in FIG. 3, intravascular tissue growth mechanically connects collars 30, 32 and 34 to the lumen. Barbs 42 may mechanically connect stent-graft 36 to the collars, and subsequent intravascular tissue growth may further strengthen that mechanical connection. These mechanical connections, as well as the enhanced surface contact that the uniform landing areas of the collar stents provide, help to more securely fix stent-graft 36 to the lumen than implantation of the stent-graft without the collar stents. This more secure fixation is desirable not just in applications where fixation may be problematic because of morphology, but also even in standard morphologies. In particular, the more secure fixation may prevent migration of the stent after changes in anatomy subsequent to implantation of the stent-graft. In particular, the system of the present invention may reduce neck migration.

Figure 6:
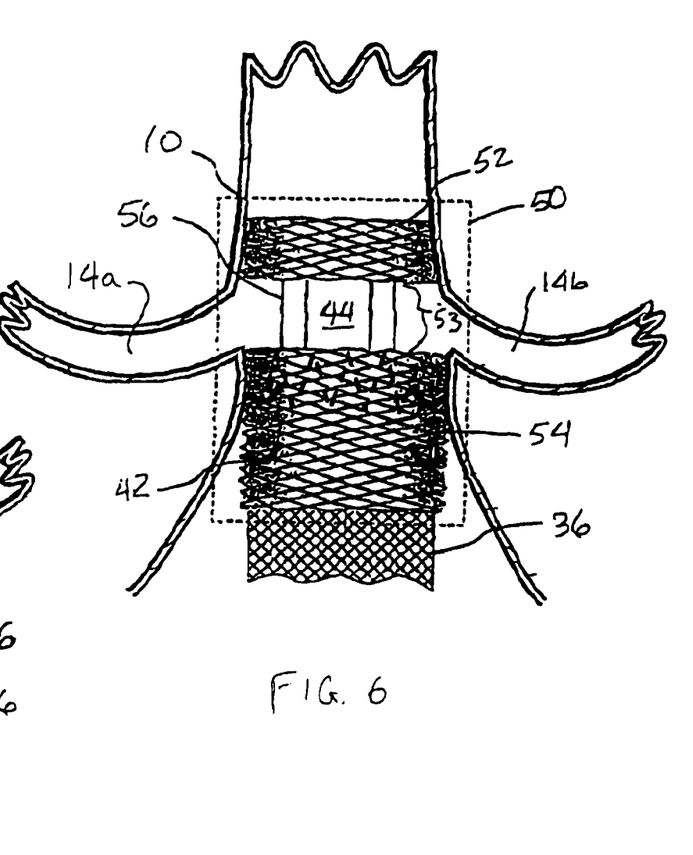
FIG. 6 shows a distal portion of an aorta in longitudinal section with an exemplary bridging collar stent deployed therein.

Referring now to FIG. 6, in other applications, it may be desirable to increase the amount of fixation area even more than just through intravascular tissue growth. Renal bridging collar stent 50 comprises a first upper section 52, a second, intermediate section 53, and a third, lower section 54. Upper and lower sections 52 and 54 each have a dense architecture with a relatively low percentage of open area between filaments, and may have essentially the same or similar architecture. Intermediate section 53 typically has a greater percentage of open area than the upper or lower sections. As shown in FIG. 6, intermediate section 53 merely comprises a plurality of bridging struts 56 that connect upper section 52 to lower section 54.

"Percentage of open area" as used herein may be defined as:

$$\frac{A_s - \sum A_{fp}}{A_s} = \frac{(\pi D_s L_s - \sum D_f L_f)}{\pi D_s L_s}$$

where:
$L_s$=the length of the stent portion at issue
$D_s$=the diameter of the stent
$A_s$=the cylindrical surface area of the stent ($\pi D_s L_s$)
$D_f$=the diameter of the filament
$L_f$=the length of the filament contained within length $L_s$
$\Sigma A_{pf}$=the "projected" rectangular area ($D_f L_f$) of each filament onto $A_s$
It should be noted that the projected area $A_{fp}$ is not the same as the actual surface area of each filament length $L_f$, which is equal to projected area $A_{fp}$ times $\pi$.

As shown in FIG. 6, lower section 54 has barbs but upper section 52 does not. This is because the endoluminal device only attaches to lower section 54. In an alternate embodiment, such as where the endoluminal device is also adapted to bridge the intersecting lumens and thus attaches to both the upper and lower sections of the bridging collar, the upper section may also have barbs. Although shown implanted across the renal intersection 44 in FIG. 6, bridging collar stent 50 may be designed for application in any lumen where there is one or more intersecting lumens desired not to be blocked, so that blood or other endoluminal fluid can continue to flow to or from the intersecting lumens. The length of intermediate section 53 may vary depending on the lumen geometry, but is any length that is sufficient to allow fluid flow into the intersecting lumen or lumens.

The collar stents may comprise one or more braided filaments, a filament bent into a pattern, or a cut tube, a multitude of geometries and architectures for which are well-known in the art. The collar stents may comprise any material known in the art for stents, such as, for example, nitinol or stainless steel. It may be particularly desirable for the collar stents to comprise a radiopaque material that is readily detected by viewing devices. A radiopaque material is one that has a radiographic density higher than the material of surrounding host tissue into which it is implanted and that has a thickness sufficient to affect the transmission of x-rays to produce contrast in the image. Collar stents comprising metals including tantalum or platinum, which have relatively high radiographic densities, may be particularly advantageous, but other metals such as stainless steel, superalloys, nitinol, and titanium having lower radiographic densities may also be used. A clad composite stent disclosed by U.S. Pat. No. 5,630,840 to David Mayer, assigned to Schneider (USA) Inc., and incorporated herein by reference, may be particularly advantageous. The collar stents may instead or additionally comprise one or more radiopaque markers as are known in the art.

The enhanced visibility provided by collar stents that have sufficient radiopacity to be viewed with even less than state-of-the-art viewing equipment, may improve the precision with which the ensuing endoluminal device can be placed. Thus, instead of implanting an endoluminal device into a body lumen which is difficult to see, the surgeon installing an endoluminal device radially within one or more collar stents of this invention has enhanced vision of the landing point or points for the device. Furthermore, the collar stents provide readily visible landmarks for post-implantation measurement procedures for tracking the morphology of the repaired area.

Figure 7A:
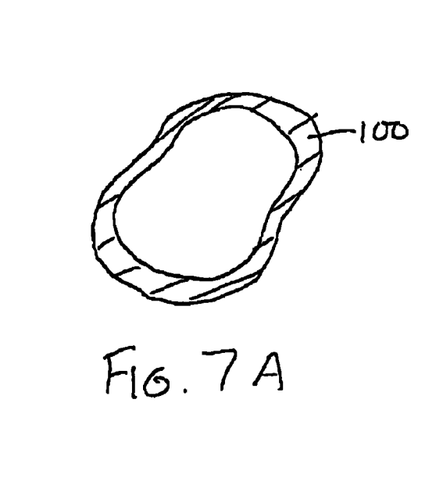
FIG. 7A shows a lumen having a non-circumferential cross-section.
Figure 7B:
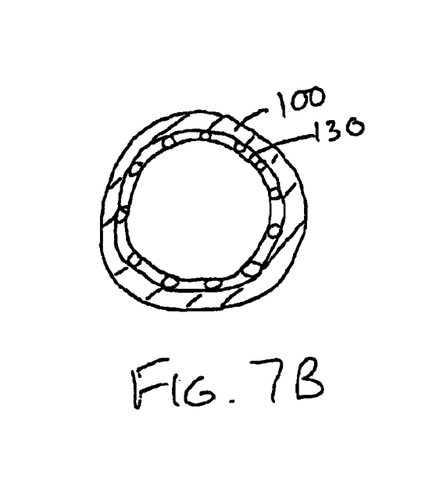
FIG. 7B shows the lumen of FIG. 7A after implantation of an exemplary collar stent of this invention.
Figure 8A:
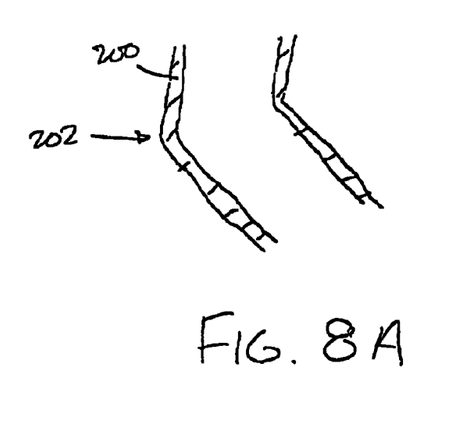
FIG. 8A shows a lumen, in longitudinal section, having an angled inflection.
Figure 8B:
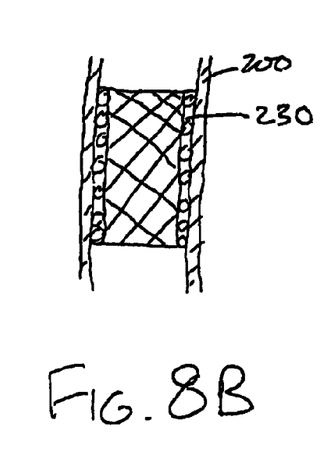
FIG. 8B shows the lumen of FIG. 8A after implantation of an exemplary collar stent of this invention.

The collar stents of this invention may be deployable by any mechanism, and may be self-expandable from a radially compressed configuration to a radially expanded configuration by spring elasticity or by thermal or stress-induced return of a shape memory material, or may be balloon expandable. Regardless of the expansion mechanism, the collar stent preferably has sufficient radial strength to change the morphology of the lumen into which it is implanted to a more favorable morphology. For example, lumen 100 has a non-circumferential morphology, as shown in FIG. 7A, which may be caused by calcification or other reasons. As shown in FIG. 7B, collar stent 130 has sufficient radial strength to deform lumen 100 to a more circumferential morphology. For morphologies with an angular inflection point 202 in lumen 200, as shown in FIG. 8A, collar stent 230 has sufficient radial strength to straighten the lumen, as shown in FIG. 8B. It should be understood that the essence of FIGS. 7A-7B are to show that the morphology is improved by the implantation of a collar stent of this invention, and that actual morphology improvements may be more or less exaggerated than as depicted.

Furthermore, although illustrated and described herein with reference to certain specific embodiments, the present invention is nevertheless not intended to be limited to the details shown. Rather, various modifications may be made in the details within the scope and range of equivalents of the claims and without departing from the spirit of the invention. For example, although illustrated and described herein predominantly with respect to AAA stent graft and branching lumen applications generally, it should be understood that the apparatus and methods of this invention may be useful in any lumen, vascular or non-vascular, non-branched, bifurcated, or having multiple branches.

What is claimed:

1. A system for implantation in a lumen, the system comprising:
an endoluminal device; and a distal collar stent that preconditions a portion of the lumen and anchors the endoluminal device, wherein preconditioning comprises the distal collar stent being configured to promote intravascular tissue growth around the distal collar stent to strengthen an anchor location at a distal end of an aneurysm;
the endoluminal device having at a distal portion that deploys radially within the distal collar stent after deployment of the distal collar stent in the lumen at the distal end of the aneurysm, wherein the distal collar stent only covers the distal portion of the endoluminal device at the distal end of the aneurysm, wherein the endoluminal device has a distal end and a proximal end, and the system comprises the distal collar stent that aligns with and completely surrounds the distal end.

2. The system of claim 1, wherein the endoluminal device comprises a stent-graft.

3. The system of claim 2, wherein the system comprises a second collar stent that aligns with the proximal end.

4. The system of claim 2, wherein the stent-graft has a distal end and branches into at least two proximal portions, each portion having a proximal end, wherein the distal collar stent aligns with the distal end, a second collar stent that aligns with a first proximal end, and a third collar stent that aligns with a second proximal end.

5. The system of claim 4, wherein the stent-graft deploys in an aorta having a main body, one or more renal arteries that branch off of the main body at a renal intersection, a neck downstream of the renal intersection, and two iliac arteries that branch from the main body, the distal collar stent deploys in the neck, the second collar stent deploys in one of the iliac arteries, and the third collar stent deploys in another of the iliac arteries.

6. The system of claim 5, wherein the distal collar stent comprises a first region having a first stent geometry with a first percentage of open area, a second region having a second stent geometry with a second percentage of open area greater than the first percentage, and a third region having the third stent geometry with a third percentage of open area less than the second percentage, the second region located intermediate the first region and the third region, the second region having a length sufficient to bridge the renal intersection.

7. The system of claim 6, wherein the second stent geometry comprises a set of bridging struts.

8. The system of claim 6, wherein the third stent geometry is essentially identical to the first stent geometry.

9. The system of claim 1, wherein the distal collar stent comprises a first region having a first stent geometry with a first percentage of open area, a second region having a second stent geometry with a second percentage of open area greater than the first percentage, and a third region having the third stent geometry with a third percentage of open area less than the second percentage, the second region located intermediate the first region and the third region.

10. The system of claim 9, wherein second stent geometry comprises a set of bridging struts.

11. The system of claim 9, wherein the third stent geometry is essentially identical to the first stent geometry.

12. The system of claim 1, wherein the distal collar stent comprises a plurality of barbs that protrude radially inward from the stent for engaging the endoluminal device.

13. The system of claim 1, wherein the distal collar stent is radiopaque.

14. The system of claim 1, wherein the distal collar stent has a radial strength sufficient to modify a morphology of the lumen into which it is implanted.

15. The system of claim 14, wherein the radial strength is sufficient to change a non-circumferential morphology to a circumferential morphology, change an angularly inflected morphology to a straight morphology, or both.

16. The system of claim 1, wherein the distal collar stent is uncoated.

17. The system of claim 1, wherein the distal collar stent is coated with a material that encourages intravascular tissue growth.

18. The collar stent of claim 1, wherein the first lumen is an aorta and an intersecting lumen are renal arteries that intersect the aorta at a renal intersection, in which a collar stent intermediate region length is sufficient to bridge the renal intersection.

* * * * *